United States Patent
Zysman et al.

[11] Patent Number: 5,539,129
[45] Date of Patent: Jul. 23, 1996

[54] NONIONIC AMPHIPHILIC COMPOUNDS DERIVED FROM GLYCEROL, A PROCESS FOR PREPARING THEM, AND CORRESPONDING INTERMEDIATE COMPOUNDS

[75] Inventors: Alexandre Zysman; Henri Sebag; Alain Ribier, all of Paris; Guy Vanlerberghe, Villevaude; Claude Mahieu, Paris; Claude Berthelot, Les Pavillons Sous Bois, all of France

[73] Assignee: L'Oreal, Paris, France

[21] Appl. No.: 278,961

[22] Filed: Jul. 22, 1994

Related U.S. Application Data

[62] Division of Ser. No. 910,174, Jul. 14, 1992, Pat. No. 5,362,494, filed as PCT/FR91/00889, Nov. 13, 1991.

[30] Foreign Application Priority Data

Nov. 14, 1990 [FR] France ................................. 90 14149
Aug. 8, 1991 [FR] France ................................. 91 10128

[51] Int. Cl.$^6$ ......................... C07C 43/11; C07C 43/30; C07D 317/00
[52] U.S. Cl. ......................... 549/430; 252/309; 252/312; 252/351; 568/591; 568/608; 568/619
[58] Field of Search ..................... 252/351, DIG. 1; 568/608, 619, 591; 514/975; 549/518, 521, 430, 497, 502

[56] References Cited

U.S. PATENT DOCUMENTS

| | | | |
|---|---|---|---|
| 3,463,745 | 8/1969 | Hofrichter et al. | 568/608 X |
| 3,748,276 | 7/1973 | Schmolka | 252/351 X |
| 3,821,372 | 6/1974 | Vanlerberghe et al. | 514/941 X |
| 3,998,948 | 12/1976 | Vanlerberghe et al. | 514/944 X |
| 4,086,279 | 4/1978 | Langdon et al. | 252/351 X |
| 4,105,580 | 8/1978 | Sebag et al. | 252/351 |
| 4,115,314 | 9/1978 | Oppenlaender et al. | 252/351 X |
| 4,224,311 | 9/1980 | Vanlerberghe et al. | 514/941 X |
| 4,282,387 | 8/1981 | Olstowski et al. | 568/618 |
| 4,657,556 | 4/1987 | Sebag et al. | 514/941 X |
| 4,670,185 | 6/1987 | Fujiwara et al. | 428/402.2 X |
| 4,677,232 | 6/1987 | Sebag et al. | 568/619 |
| 4,703,114 | 10/1987 | Mori et al. | 568/608 X |
| 4,830,857 | 5/1989 | Handjani et al. | 424/450 |
| 4,832,868 | 5/1989 | Schmid et al. | 252/351 X |
| 4,897,308 | 1/1990 | Vanlerberghe et al. | 428/402.2 |
| 4,954,345 | 9/1990 | Müller | 424/450 |
| 4,963,535 | 10/1990 | Sebag et al. | 514/941 X |
| 5,213,802 | 5/1993 | Masten | 424/450 X |
| 5,227,470 | 7/1993 | Kanno et al. | 424/450 X |
| 5,243,086 | 9/1993 | Jakobson et al. | 568/619 |
| 5,362,494 | 11/1994 | Zysman et al. | 424/401 |

FOREIGN PATENT DOCUMENTS

| | | |
|---|---|---|
| 0066107 | 12/1982 | European Pat. Off. . |
| 0071019 | 2/1983 | European Pat. Off. . |
| 0283165 | 9/1988 | European Pat. Off. . |
| 2144122 | 2/1985 | United Kingdom . |

*Primary Examiner*—Richard D. Lovering
*Attorney, Agent, or Firm*—Cushman Darby & Cushman

[57] ABSTRACT

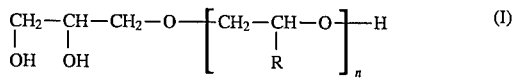

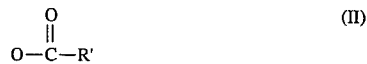

Non-ionic amphiphilic, glycerol-derived compounds having formula (I), where R is a radical selected from the group consisting of $C_{4-28}$ branched or linear alkenyl or alkyl radicals or mixtures thereof, or is a —$CH_2A$ grouping in which A is —OR', —SR, (II) where R' is a saturated or unsaturated hydrocarbonated radical and n represents an average statistical value n greater than 1 and equal to or less than 6; and, when R' is a —$CH_2A$ radical, n is also 2. These compounds are surface-active agents and some may form vesicles.

12 Claims, No Drawings

NONIONIC AMPHIPHILIC COMPOUNDS DERIVED FROM GLYCEROL, A PROCESS FOR PREPARING THEM, AND CORRESPONDING INTERMEDIATE COMPOUNDS

This is a division of application Ser. No. 07/910,174, filed as PCT/FR91/00889, Nov. 13, 1991, now U.S. Pat. No. 5,362,494.

The invention relates to nonionic amphiphilic compounds derived from glycerol containing several lipophilic chains, to a process for preparing them, to intermediate compounds in the preparation of said amphiphilic compounds obtained in said preparation process and to compositions containing said compounds.

Nonionic amphiphilic compounds of glycerol containing only one lipophilic chain attached to a hydrophilic chain, and which are of the formulae:

$$R_1O + C_2H_3O(CH_2OH) \overline{\tfrac{1}{n}} H \quad (A)$$

in which $R_1$ is an alkyl radical and n is a number below 10, and

$$R_2-O+C_2H_3O(CH_2OCH_2-CHOH-CH_2OH) \overline{\tfrac{1}{n}} H \quad (B)$$

where $R_2$ is an alkyl radical and n is a number not exceeding 5, are already known from French Patents 1,477,048 and 1,484,723.

Nonionic amphiphilic compounds derived from glycerol containing two lipophilic chains, which are of the formula

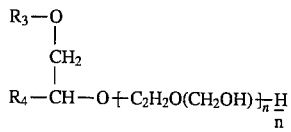

where $R_3$ and $R_4$ can be alkyl radicals and $\bar{n}$ is an average statistical value between 2 and 20 are also known from French Patent 2,482,128.

These known compounds may be used as surfactant agents, as emulsifying agents or, in the case of the compounds of formulae (A) and (C), for the manufacture of nonionic vesicles.

The compound of formula (E) containing a single lipophilic chain:

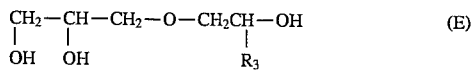

in which formula $R_3$ is a $C_{14}$ or $C_{15}$ hydrocarbon radical, is known from the paper by MURAMATSU and SCHMID (Chem. Phys. Lipids 1972,9(2), p.123–132).

The present invention relates to nonionic amphilic compounds derived from glycerol, characterized in that they are of the formula (I):

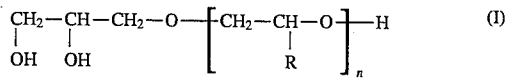

in which formula R represents a radical taken from the group composed of linear or branched $C_4$–$C_{28}$ alkyl or alkenyl radicals and mixtures thereof, or represents a group —$CH_2A$ in which A represents —OR', —SR' or

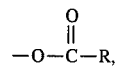

R' representing a saturated or unsaturated hydrocarbon radical, and n represents an average statistical value $\bar{n}$ greater than 1 and equal to not more than 6 and, when R is —$CH_2A$, n is also a value equal to 2. The hydrocarbon radical R' is preferably a linear $C_8$–$C_{22}$ alkyl radical, a branched $C_8$–$C_{36}$ alkyl radical, a $C_{18}$ alkenyl radical or an alkylaryl radical having a linear or branched $C_8$–$C_{16}$ alkyl chain; in the alkylaryl radical, the aryl group is preferably a phenyl group; the alkenyl radical is advantageously a 9-octadecenyl or 9,12-octadecanedienyl radical. When R is —$CH_2A$, A is preferably OR'.

Preferred compounds of formula (I) are those in which R represents a linear $C_{14}$–$C_{18}$ alkyl radical or a group —$CH_2A$ in which A is OR', R' representing a linear $C_{10}$–$C_{18}$ radical, and n represents an average statistical value $\bar{n}$ greater than 1 and equal to not more than 3 and, when R represents —$CH_2A$, is also a value equal to 2.

The subject of the present invention is also the preparation of the compounds of formula (I) by a two-stage process with formation of intermediate product(s), characterized in that:

—in a first stage, isopropylideneglycerol of formula (IV) is reacted in the presence of a basic catalyst with an epoxide of formula (III), in which R has the same meaning as in the formula (I), to obtain one or more intermediate product(s) of formula (II) according to the following reaction scheme:

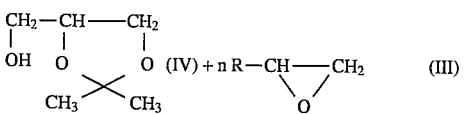

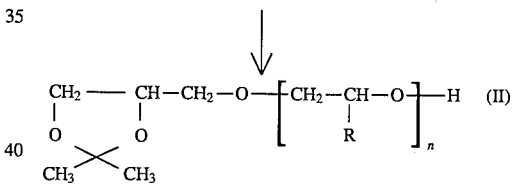

R and n having the same meaning as in the formula (I), and

—in a second stage, the intermediate product(s) of formula (II) obtained is/are hydrolyzed and the compound(s) of formula (I) is/are separated from the reaction mixture.

In the first stage of the preparation process, the basic catalyst used is preferably chosen from the group composed of alkali metals, alkali metal hydrides, alkali metal hydroxides, alkali metal alcoholates, amines and alkali metal fluorides such as KF, RbF and CsF, these fluorides preferably being absorbed on alumina. An alkali metal alcoholate, especially potassium tert-butylate, is preferably used. The amount of basic catalyst used is advantageously between 0.5 and 100 mol %, and preferably between 4 and 40 mol %, relative to the isopropylidene-glycerol of formula (IV).

In the first stage, it is preferable to work in the manner described below. At least a part of the isopropylideneglycerol of formula (IV) and the basic catalyst are first mixed under an inert atmosphere, for example under a nitrogen atmosphere, and the mixture is heated to a temperature of between 50° and 190° C., and preferably in the region of 150° C. The mixing is preferably performed in the absence of solvent, but solvents such as dimethylformamide or methylpyrrolidone may be used.

To the mixture obtained, the epoxide of formula (III), where appropriate dissolved in the remainder of the isopropylideneglycerol of formula (IV), is added. This addition may be performed either all at once, or gradually, generally over a period of between 30 minutes and 2 hours.

In the second stage, the intermediate product(s) obtained, of formula (II), is/are then hydrolyzed. This hydrolysis is preferably performed in the presence of an acid catalyst. The latter can be an inorganic acid such as hydrochloric, hydrofluoric, sulfuric or phosphoric acids or an organic acid such as acetic or oxalic acid. The hydrolysis reaction is preferably performed at a temperature of between 25° C. and 100° C.

A solvent may be used to perform the hydrolysis reaction. This solvent is, for example, methanol, ethanol, isopropanol, heptane, hexane, acetone, ethers such as ethyl ether or isopropyl ether or glycol mono- or diethers such as diglyme.

After the hydrolysis reaction, the mixture is filtered and the filtrate is then heated under reduced pressure to remove volatile products and collect the compound(s) of formula (I).

The subject of the present invention is also, as a new industrial product, the nonionic intermediate compounds of formula (II) obtained in the first stage of the process for preparing the compounds of formula (I).

The compounds of formula I according to the invention may be used for the preparation of cosmetic or pharmaceutical compositions, especially dermopharmaceutical compositions.

All the compounds of formula I are surfactants. They may hence be used as such in the compositions. They may consequently be used as dispersing agents, emulsifying agents or washing agents.

The subject of the present invention is hence a cosmetic or pharmaceutical composition containing at least one compound of formula I, used as a surfactant. One or more compounds of formula I may be used as a surfactant agent, or they may be used in combination with conventional surfactant agents.

In a known manner, the cosmetic or pharmaceutical compositions can be oily compositions in the form of a liquid, a gel or solids of waxy appearance. In these compositions, the compounds of formula I are advantageously used as dispersants.

These compositions can also be water-in-oil or oil-in-water type emulsions, in which the compounds of formula I may be used as an emulsifying agent. One or more compounds of formula I may be combined with other, conventional emulsifying agents such as polyoxyethylenated fatty acids or fatty alcohols, polyglycerol alkyl ethers, esters of fatty acid and sorbitan, polyoxyethylenated or otherwise, esters of fatty acid and sorbitol, polyoxyethylenated or otherwise, polyoxy-ethylenated castor oil, salts of fatty acids and amines or polyvalent metals, alkyl sulfates, polyoxyethylenated or otherwise, and alkyl phosphates, polyoxyethylenated or otherwise.

In a known manner, the fatty phase of the emulsions used in cosmetics or in pharmacy essentially contain oils or waxes. Among oils, there may be mentioned, without implied limitation, mineral oils such as vaseline, animal oils such as whale, seal, halibut liver, cod liver, tuna and mink oils, vegetable oils such as almond, groundnut, wheat germ, maize, olive, jojoba, sesame and sunflower oils, and silicone oils. Among waxes, there may be mentioned, without implied limitation, sipol wax, lanolin, hydrogenated lanolin, acetylated lanolin, beeswax, candellila [sic] wax, microcrystalline wax, paraffin wax, carnauba wax, spermaceti, cocoa butter, shea butter, silicone waxes and hydrogenated oils which are solid at 25° C. The oils and waxes may also be chosen from the esters of saturated or unsaturated $C_{12}$ to $C_{22}$ fatty acids and of lower polyols or alcohols such as isopropanol, glycol or glycerol, or of saturated or unsaturated, linear or branched $C_8$–$C_{22}$ fatty alcohols, or alternatively of $C_{10}$–$C_{22}$ 1,2-alkanediols.

The compositions in which the compounds of formula I are used as surfactants preferably contain from 0.5 to 50%, and more generally from 0.5 to 25%, by weight of compound of formula I relative to the total weight of the composition.

In the compositions according to the invention, the products or mixtures of compounds (I) may be combined with other ionic or nonionic surfactants, with natural or synthetic, ionic or nonionic polymers, with oils or waxes, with more or less hydrolyzed proteins, with thickeners, with pearlescent agents, with emollients, with hydrating agents, with colorants, with reducing or oxidizing agents, with preservatives, with perfumes, with anti-UV screening agents, with solvents, with propellants or with pharmaceutical or parapharmaceutical active products.

Some compounds of formula (I), especially those in which R represents a linear $C_{14}$–$C_{18}$ alkyl radical or represents —$CH_2A$, A being —OR' and R' representing a linear $C_{10}$–$C_{18}$ alkyl radical, and n represents an average statistical value $\bar{n}$ greater than 1 and equal to not more than 3 and, when R represents —$CH_2A$, is also equal to 2, are nonionic amphiphilic lipids capable of forming vesicles having a lamellar structure.

In a known manner, these vesicles are characterized by a lamellar structure consisting of layers of lipid phase encapsulating an aqueous phase.

These vesicles are, in a known manner, prepared in the form of a dispersion in an aqueous phase. A non-limiting list of various methods of preparation will be found in "Les liposomes en biologie celullaire et pharmacologie" [Liposomes in cell biology and pharmacology] Editions INSERM/John Libbey Eurotext, 1987, pages 6 to 18.

The vesicles obtained hence consist of a lipid phase consisting of one or more lamellae encapsulating a phase E, and they are dispersed in an aqueous dispersion phase D.

The vesicles formed with the compounds of formula (I) for which R represents a linear $C_{14}$–$C_{18}$ alkyl radical or represents —$CH_2A$, A being —OR' and R' representing a linear $C_{10}$–$C_{18}$ alkyl radical, and n represents an average statistical value $\bar{n}$ greater than 1 and equal to not more than 3 and, when R represents —$CH_2A$, is also equal to 2, possess, in the main, a good degree of swelling, low permeability and good stability. Surprisingly, the preferred compounds of formula (I) for which R represents a linear $C_{14}$ alkyl group or a group —$CH_2A$, A being —OR' and R' representing a linear $C_{16}$ alkyl group, enable vesicle dispersions having a higher viscosity than that obtained using the compounds of formula (A) defined above, containing a single lipophilic chain, to be obtained in the presence of a cosmetic vehicle. In effect, the cosmetic active compounds commonly introduced into vesicular phases are known to have a fluidizing effect and to bring about a fall in viscosity of the compositions.

The use of these dispersions of vesicles obtained with the preferred compounds of formula (I) hence make it possible to prepare thick creams, rich in active principles, by limiting the fluidizing effect of the cosmetic active compounds.

The subject of the present invention is hence also a cosmetic or pharmaceutical composition containing, dispersed in an aqueous phase D, vesicles bounded by one or more lamellae formed from a lipid phase containing at least one compound of formula (I) in which R represents a linear $C_{14}$–$C_{18}$ alkyl radical, preferably a linear $C_{14}$ alkyl radical, or represents —$CH_2A$, A being OR' and R' representing a linear $C_{10}$–$C_{18}$ alkyl radical, preferably a linear $C_{16}$ alkyl radical, and n represents an average statistical value $\bar{n}$ greater than 1 and equal to not more than 3 and, when R is —$CH_2A$, is also equal to 2.

In a known manner, other ionic amphiphilic lipids and/or nonionic amphiphilic lipids may be combined in the lipid phase with the nonionic amphiphilic lipids of formula (I).

The ionic amphiphilic lipids which may be mixed in the lipid phase with the amphiphilic lipids of formula (I) are preferably chosen from the group composed of natural phospholipids, modified chemically or enzymatically, or synthetic phospholipids, anionic compounds and gangliosides.

Among natural phospholipids, egg or soybean lecithin and sphingomyelin may be mentioned; among synthetic phospholipids, dipalmitoylphosphatidylcholine may be mentioned, and among modified phospolipids, hydrogenated lecithin may be mentioned.

Among anionic compounds, there may be mentioned those which are represented by the formula:

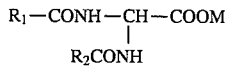

in which formula:

$R_1$ represents a $C_7$–$C_{21}$ alkyl or alkenyl radical;

$R_2$ represents a saturated or unsaturated $C_7$–$C_{31}$ hydrocarbon radical; and M represents H, Na, K, $NH_4$ or a substituted ammonium ion derived from an amine.

The nonionic amphiphilic lipids which may be mixed in the liquid phase with the amphiphilic lipids are preferably chosen from the group composed of:

(1) linear or branched polyglycerol derivatives of formula:

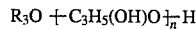

in which:

—$C_3H_5(OH)O$— is represented by the following structures, taken mixed or separately:

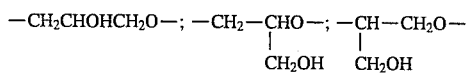

$\bar{n}$ is an average statistical value between 2 and 6;

$R_3$ represents:

(a) a saturated or unsaturated, linear or branched aliphatic chain containing from 12 to 30 carbon atoms; or the hydrocarbon radicals of lanolin alcohols;

(b) a residue $R'_3CO$, where $R'_3$ is a linear or branched $C_{11}$–$C_{17}$ aliphatic radical;

(c) a residue

where $R_4$ can take the meaning (a) or (b) given for $R_3$;

—$OC_2H_3(R_5)$— is represented by the following structures, taken mixed or separately:

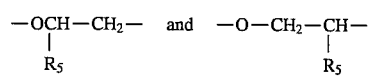

where $R_5$ takes the meaning (a) given for $R_3$;

(2) linear or branched polyglycerol ethers containing two fatty chains;

(3) polyoxyethylenated fatty alcohols and polyoxyethylenated sterols and phytosterols;
(4) polyol ethers;
(5) polyol esters, oxyethylenated or otherwise;
(6) glycolipids of natural or synthetic origin;
(7) hydroxyamides represented by the formula:

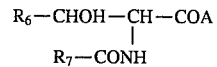

in which:

—$R_6$ denotes a $C_7$–$C_{21}$ alkyl or alkenyl radical;

—$R_7$ denotes a saturated or unsaturated $C_7$–$C_{31}$ hydrocarbon radical;

—COA denotes a group chosen from the following two groups:

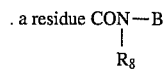

where

B is a radical derived from mono- or polyhydroxylated primary or secondary amines; and $R_8$ denotes a hydrogen atom or a methyl, ethyl or hydroxyethyl radical; and a residue —COOZ, where Z represents the residue of a $C_3$–$C_7$ polyol.

In the polyglycerol derivatives, the saturated linear aliphatic radical $R_3$ is preferably a lauryl, myristyl, cetyl, stearyl, arachidyl, behenyl or ligno-ceryl radical or a mixture of these radicals; and the unsaturated aliphatic radical $R_3$ is advantageously a palmitoleyl, oleyl, linoleyl or arachidonyl radical.

The compounds defined in point (3) above are advantageously $C_{12}$–$C_{22}$ alcohols bearing 2 to 20 ethylene oxide (EO) units. The sterol is advantageously cholesterol; it may be substituted with 2 to 20 EO units. Similarly, the phytosterol may be substituted with 2 to 20 mol of EO.

The polyol ethers defined in point (4) above are preferably alkyl ethers of $C_2$–$C_7$ polyols.

The polyol esters defined in point (5) above are advantageously sorbitol esters.

The glycolipids which can be used as nonionic amphiphilic lipids are advantageously cerebrosides.

At least one additive which enables the permeability of the vesicles to be decreased, and/or at least one charged lipid intended for improving the stability of the vesicles by preventing their flocculation and their fusion and for enabling the degree of encapsulation to be increased, may advantageously be incorporated in a known manner in the lipid phase.

Among these additives or charged lipids which can be used, there may be mentioned, in particular:

—sterols and their derivatives, for example oxyethylenated derivatives, more especially cholesterol, cholesterol acid sulfate and its alkali metal salts and cholesterol acid phosphate and its alkali metal salts;
—long-chain alcohols and diols;
—long-chain amines and their quaternary ammonium derivatives;
—dihydroxyalkylamines;
—polyoxyethylenated fatty amines;
—esters of long-chain amino alcohols and their salts and quaternary ammonium derivatives;
—phosphoric esters of fatty alcohols, for example dicetyl phosphate and dimyristyl phosphate in the form of acids or of alkali metal salts.

The compositions obtained with the compounds according to the invention can contain, in a known manner, one or more active compound(s) having cosmetic and/or dermopharmaceutical activity, which, depending on their solubility properties, can have different localizations. For example, in the case of dispersions of vesicles containing an encapsulated aqueous phase, if the active compounds are fat-soluble, they are introduced into the lipid phase constituting the lamella(e) of the vesicles; the active compounds are water-soluble, they are introduced into the encapsulated aqueous phase of the vesicles; if the active compounds are amphiphilic, they distribute between the lipid phase and the encapsulated aqueous phase with a partition coefficient which varies according to the nature of the amphiphilic active compound and the respective compositions of the lipid phase and of the encapsulated aqueous phase. Generally speaking, the active compounds are placed in the lipid phase of the lamellae and/or in the phase encapsulated by the lamellae.

In the case of oil-in-water or water-in-oil type emulsions containing a compound of formula I as emulsifying agent, the fat-soluble compounds are introduced into the oily phase and the water-soluble compounds into the aqueous phase. Similarly, the amphiphilic active compounds distribute between the aqueous phase and the oily phase.

Water-soluble active compounds are, for example, glycerol, sorbitol, erythrulose and antibiotics; fat-soluble active compounds are, for example, retinoic acid, lipoprotides and steroids.

The active compounds introduced can have a wide variety of cosmetic and/or dermopharmaceutical activities (or "functions") which are given in the table below.

TABLE

| FUNCTION | ACTIVE COMPOUNDS WHICH CAN BE USED |
|---|---|
| Antioxidant or free-radical inhibitor | Extracts of the following plants: Hawthorn. Ginkgo biloba. Green tea. Grapevine. Rosemary Enzymes: Marketed by SEDERMA under the name SB 12 and consisting of a mixture of lactoferrin and lactoperoxidase, glucose oxidase and potassium thiocyanate. Superoxide dismutase. Glutathione peroxidase. Superphycodismutase extracted from algae. Coenzymes Q, especially coenzyme Q10. Sequestering agents, especially polyphosphonic acid derivatives. Tannins. Selenium and its derivatives, especially seleniomethionine. Peptides, for example a mixture of spleen and thymus extracts. Thiolim and unstabilized bovine serum albumin. Proteins, for example hemocyanin which is a copper-containing protein extracted from the marine snail, and apohemocyanin which is a similar protein without copper. Flavonoids, in particular catechin, |

TABLE-continued

| FUNCTION | ACTIVE COMPOUNDS WHICH CAN BE USED |
|---|---|
| | proanthocyanidins, flavanols, flavones, isoflavones, flavanenols, flavanones, flavans and chalcones. Carotenoids, in particular β-carotene and annatto. Sorbohydroxyamic acid. Tocopherols, in particular alpha-tocopherol and alpha-tocopherol acetate. Ascorbyl palmitate. Propyl gallate. Caffeic acid and its derivatives. Ascorbic acid. Homogentisic acid. Erythorbic acid. Nordihydroguaiacetic acid. Lysine laurylmethionate. Butylated hydroxyanisole. Butylated hydroxytoluene. "SOD-like" substances. |
| Hydrating or humectant | A reconstitution of sweat ("Normal moisturizing factors" -NMF). Sodium pyroglutamate. Hyaluronic acid. Chitosan derivatives (carboxymethylchitin). β-Glycerophosphate. Lactamide. Acetamide. Ethyl, sodium and triethanolamine lactates. Metal pyrrolidonecarboxylates, especially of Mg, Zn, Fe or Ca. Thiamorpholinone. Orotic acid. $C_3$ to $C_2$ alpha-hydroxylated carboxylic acids, in particular alpha-hydroxypropionic acid. Polyols, in particular inositol, glycerol, diglycerol, sorbitol. Saccharide polyols, in particular alginate and guar. Proteins, in particular soluble collagen and gelatin. Lipoprotides chosen from mono- or polyacylated derivatives of amino acids or of polypeptides in which the acid residue RCO contains a $C_{13}$–$C_{19}$ hydrocarbon chain, in particular palmitoylcaseinic acid, palmitoylcollagenic acid, the O,N-dipalmitoyl derivative of hydroxyproline, sodium stearoylglutamate, the stearoyl tripeptide of collagen, the oleyltetra-and, pentapeptide of collagen, hydroxyproline linoleate. Urea and its derivatives, in particular methyl urea. Cutaneous tissue extract, in particular that marketed by Laboratoires Serobiologiques de Nancy (LSN) under the name "OSMODYN", containing peptides, amino acids and saccharides and 17% of mannitol. More especially, a combination of glycerol, urea and palmitoylcaseinic acid. |
| Melanoregulator: 1) tanning accelerator | Bergamot and citrus oils. Alpha-MSH and its synthetic homologs. Caffeine. Tyrosine derivatives, in particular |

| FUNCTION | ACTIVE COMPOUNDS WHICH CAN BE USED |
|---|---|
| | glucose tyrosinate and N-malyltyrosine. |
| 2) Depigmenting | Ascorbic acid or vitamin C and its derivatives, in particular Mg ascorbylphosphate. |
| | Hydroxy acids, in particular glycolic acid. |
| | Kojic acid. |
| | Arbutin and its derivatives. |
| | Hemocyanin (copper-containing protein of the marine snail) and apohemocyanin (protein similar to the above without copper). |
| | Hydroquinone and its derivatives, in particular the monoalkyl ether and the benzyl ether. |
| Skin coloration (artificial tanning) | ortho-Diacetylbenzene. |
| | Indoles. |
| | Dihydroxyacetone. |
| | Erythrulose. |
| | Glyceraldehyde. |
| | Gamma-dialdehydes, in particular tartraldehyde. |
| Liporegulators (slimming and anti-acne, anti-seborrhea) | Complexes of vitamins and trace elements, in particular the vitamin $B_6$/zinc complex. |
| | Orizanol. |
| | Azelaic acid. |
| | Xanthines and alkylxanthines, in particular cola extract, caffeine and theophylline. |
| | Adenosine monophosphate, cyclic and non-cyclic. |
| | Adenosine triphosphate. |
| | Ivy extract. |
| | Horse chestnut extract. |
| | Extracts of algae, in particular extract of red algae (fucus serratus) and cytofiltrate. |
| | Ginseng extract. |
| | Centella Asiatica extract (asiaticoside) containing genin and asiatic acid. |
| | Thioxolone (HBT). |
| | S-Carboxymethylcysteine. |
| | S-Benzylcysteamine. |
| Anti-aging and wrinkle | Unsaponifiables, for example of anti-soybean and avocado. |
| | Unsaturated fatty acids, in particular linoleic acid and linolenic acid. |
| | Hydroxy acids, in particular glycolic acid. |
| | Growth factors. |
| | Trace element/vitamin complexes, n particular $B_6$-Zn. |
| | 5-n-Octanoylsalicylic acid. |
| | Adenosins. |
| | Retinol and its derivatives, in particular retinol acetate and retinol palmitate. |
| | Retinoids, in particular cis- or trans-retinoic acids and those described in Patents FR-A-2,570,377; EP-A-199,636; and EP-A-325,540, and European Patent Application 90/402,072. |
| | Combination of retinoids and xanthines. |
| | Hydroxyproline. |
| | Sialic acids. |
| | Extract of spleen, of thymus, Thiolim and unstabilized bovine serum albumin, sold by the company "SILAB" under the trade name "SILAB". |
| | An animal placental extract, in particular bovine placental embryonic extract in water at a concentration of 5.5% stabilized with 0.2% of exyl K100a (matrix). |
| | Proteoglycans, especially bovine tracheal cartilage proteoglycan at a concentration of 5%, stabilized (proteodermin). |
| | Colostrum. |
| | Cell-oxygenation factors, in particular octacosamol. |
| Anti-UV | UV-screening agents, in particular 2-ethylhexyl para-methoxycinnamate; benzophenone, benzylidenecamphor and their derivatives, especially 2,2',4,4'-tetrahydroxybenzophenone and 2-hydroxy-4-methoxybenzophenone-5-sulfonic acid; para-aminobenzoic acid, dipropylene glycol salicylate, octyl salicylate, the dibenzoylmethane derivatives sold under the brand names EUSOLEX 8020 or PARSOL 1789, and the products sold under the brand names EUSOLEX 232, UNIVUL T 150, UNIVUL N 539, ESCALOL 507. |
| Keratolytic | Salicylic acid and its derivatives, such as alkylsalicylic acids, in particular 5-n-octanoylsalicylic acid and N-hexadecylpyridinium 5-n-dodecanoylsalicylate. |
| | Retinoic acid. |
| | Proteolytic enzymes, in particular trypsin, alpha-chymotrypsin, papain, bromelain and pepsin. |
| | Benzoyl peroxide. |
| | Urea. |
| | Alpha-hydroxy acids. |
| Emollient Anti-inflammatory | Esters such as isopropyl adipate. |
| | Corticoids such as β-methasone 17-acetate, indomethacin, ketoprofen, flufenamic acid, ibuprofen, diclofenac, diflunisal, fenclofenac, naproxen, piroxidam and sulindac. |
| | Glycerol monostearyl ether (batyl alcohol) and glycerol monocetyl ether (chimyl alcohol). |
| | Glycyrrhetinic acid and its salts, in particular the ammonium salt. |
| | Alpha-bisabolol (chamomile extract). |
| | Shikonine. |
| | Plant extracts such as cornflower, arnica, aloe water. |
| | Meristematic tissue extracts, in particular oak root extract. |
| | Plankton. |
| Freshening | Menthol. |
| | Menthyl lactate. |
| Cicatrizing | Skin tree, mimosa tenui flora extract. |
| | Centella Asiatica extract. |
| | β-Glycyrrhetinic acid. |
| | Hydroxyproline. |
| | Arginine. |
| | A placental extract. |
| | A yeast extract. |
| | Fagaramide. |
| | N-Acetylhydroxyproline. |
| | Acexamic acid and its derivatives. |
| Vasoprotective | Flavonoids, in particular rutin |

TABLE-continued

| FUNCTION | ACTIVE COMPOUNDS WHICH CAN BE USED |
| --- | --- |
| | derivatives such as etoxarutin and sodium rutin propylsulfonate. Plant extracts, in particular oily extract of Ginkgo biloba, extract of horse chestnut (escin), of ivy (saponins) and of butcher's broom. Alpha-tocopherol nicotinate. |
| Antibacterial, antifungal | Trimethylcetylammonium bromide. Sorbic acid. Benzoyl peroxide. Cetylpyridinium chloride. Benzalkonium chloride. para-Hydroxybenzoic acid and its salts. 2-Bromo-2-nitro-1,3-propanediol. 3,4,4'-Trichlorocarbanilide. 2,4,4'-Trichloro-2-hydroxydiphenyl ether. Dehydroacetic acid. An extract of grapefruit in glycerol and propylene glycol. Chlorhexidine. Hexetidine. Hexamidine. |
| Insect repellent | Dimethyltoluamide. |
| Antiperspirant | Aluminum chlorhydrate. Aluminum chloride. Sodium/aluminum chlorhydroxy lactate complex. Zirconyl chlorhydrate. |
| Deodorant | Zinc oxide. Zinc ricinoleate. 2-Ethyl-1,3-hexanediol. Hexachlorophene. The product sold under the brand name "IRGASAN DP 300". |
| Antidandruff | Octopyrox. Omadines. Coal tar. 1-Hydroxy-4-methyl-2,4,4-trimethyl-6-pentyl-2-pyridinone (sic). Selenium sulfide. |
| Combating hair loss | Glucuronidase inhibitors. Mucopolysaccharides. Methyl or hexyl nicotinate. Forskolin. Minoxidil. Xanthines. Retinoids. |
| Hair dye | Oxidation bases and couplers. Direct dyes. Self-oxidizing dyes. |
| Hair bleaching agent | Hydrogen peroxide. |
| Reducing agent for permanent waving | Thioglycolic acid. Cysteine. Cysteamine. N-Acetylcysteine. N-Acetylcysteamine. Glycerol thioglycolate. |
| Skin and hair conditioner | Cationic polymers, cations. |

One or more of the active compounds defined above may be included, it being possible for the various active compounds all to be lipophilic, water-soluble or amphiphilic, or to belong to at least two of these categories. The active compounds introduced can have the same function or different functions. It should be noted that some active compounds have several functions.

In the composition containing vesicles dispersed in an aqueous phase, the aqueous phase of dispersion of the vesicles can also contain at least one water-soluble active compound and/or at least one amphiphilic active compound.

The aqueous dispersion phase can contain, in a known manner, a dispersion of droplets of a water-immiscible liquid, which the vesicles stabilize. Consequently, in the presence of vesicles of ionic amphiphilic lipids and/or nonionic amphiphilic lipids, it is not necessary to introduce an ordinary emulsifier.

According to the present invention, the water-immiscible liquid, which can be present in form of a dispersion in the aqueous dispersion phase, consists of any water-immiscible liquid generally known to be capable of being introduced into the aqueous phase of dispersion of vesicles of ionic or nonionic lipids, it can, in particular, be chosen from the group composed of:

—an animal or vegetable oil composed of esters of fatty acid and polyols, especially liquid triglycerides, for example sunflower, maize, soybean, gourd, grape pip, jojoba, sesame and hazel nut oils, fish oils, glycerol tricaprocaprylate, or a vegetable or animal oil of formula $R_9COOR_{10}$, in which formula $R_9$ represents the residue of a higher fatty acid containing from 7 to 19 carbon atoms and $R_{10}$ represents a branched hydrocarbon chain containing from 3 to 20 carbon atoms, for example purcellin oil;

—natural or synthetic essential oils such as, for example, eucalyptus, lavandin, lavander, vetiver, litsea cubeba, lemon, sandal-wood, rosemary, chamomile, savory, nutmeg, cinnamon, hyssop, caraway, orange, geraniol and cade oils;

—hydrocarbons such as hexadecane and paraffin oil;

—halocarbons, in particular fluorocarbons such as fluoroamines, for example perfluorotributylamine, fluorinated hydrocarbons, for example perfluorodecahydronaphthalene, fluoro esters and fluoro ethers;

—silicones, for example polysiloxanes, polydimethylsiloxanes and fluorosilicones;

—esters of an inorganic acid and an alcohol;

—ethers and polyethers.

The water-immiscible liquid can contain one or more lipophilic active compounds.

The compositions according to the invention can also contain, in a known manner, formulation additives having neither cosmetic activity nor actual dermopharmaceutical activity, but which are useful for formulation of the compositions in the form of a lotion, cream or serum. These additives are, in particular, taken from the group composed of gelling agents, polymers, preservatives, colorants, opacifiers and perfumes. Among gelling agents which can be used, there may be mentioned cellulose derivatives such as hydroxyethylcellulose, derivatives of algae such as satiagum, natural gums such as tragacanth and synthetic polymers, especially the mixtures of polyvinylcarboxylic acids marketed by the company GOODRICH under the trade name "CARBOPOL". These additives are, more especially, added in an aqueous phase, for example the aqueous phase of dispersion of vesicles or the aqueous phase of an oil-in-water or water-in-oil emulsion.

The examples given below, by way of illustration and without any implied limitation, will enable a better understanding of the invention to be gained.

In the examples below, the epoxides of formula (III) are known and described, in particular, in BEILSTEIN HANDBOOK of ORGANIC CHEMISTRY (4th edition, Fifth Supplementary Series, Volume 7—part 3, EV 17/1, pages 11 and 12 and pages 159 to 170.

The alkyl (or alkylene) glycidyl ethers (or [alkyl(or alkylene)oxymethyl]oxiranes) were prepared in a known manner by the action of epichlorohydrin on the corresponding alcohol in the presence of $BF_3$, followed by neutralization with aqueous sodium hydroxide solution (see ULBRICHT et al., COLLECT. CZECH. CHEM. COMM. 29 (1964), pages 1466, 1467, 1473).

The epoxides of formula (III) for which R is an alkyl radical can, in particular, be prepared from olefins by reaction with monoperoxyphthalic acid according to EDDY et al. (Journal of America Oil Chemical Society, 40, (1963), page 92). These products are also industrially available, pure or mixed, in particular from the companies PEROXID CHEMIE G.m.b.H. (Munich) or VIKING CHEMICAL COMPANY (Minneapolis).

In the examples given below, $\bar{n}$ represents an average statistical value and n an exact value.

EXAMPLES 1 TO 20: PREPARATION OF COMPOUNDS OF FORMULA I

EXAMPLE 1: PREPARATION OF THE COMPOUND OF FORMULA

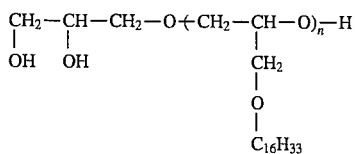

where $\bar{n}=2$.

The procedure is as follows:

1st stage 2.3 g (0.02 mol) of potassium tert-butylate are introduced into a reactor and dissolved in 19.5 g (0.145 mol) of isopropylideneglycerol, heating the mixture to 150° C. under nitrogen. 86.43 g (0.29 mol) of molten hexadecyl glycidyl ether or (hexadecyloxymethyl) oxirane of formula:

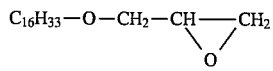

are then introduced at a constant rate in the course of two hours while the temperature is maintained at 150° C. After the addition is complete, heating is continued for 2 hours.

After neutralization and washing with water, a crude mixture containing an intermediate product of formula:

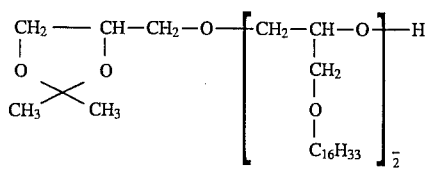

is obtained, the mixture having a melting point of 32° C.

2nd stage

The crude mixture obtained in the first stage is allowed to cool to 60° C., and 400 ml of isopropanol are then added. The temperature of the solution is adjusted to 40° C. 12 ml of 6N aqueous hydrochloric acid solution are then added and the reaction mixture is maintained for two hours at 40° C. The mixture obtained is filtered and then concentrated in a rotary evaporator at 80° C. under reduced pressure in order to remove the isopropanol.

The pasty product obtained is allowed to cool, and solidifies at room temperature. 98 g of a light yellow wax are obtained, having a melting point of 54.2° C.

Analysis by supercritical fluid chromatography and flame ionization detection shows that the product has the following composition (the percentages corresponding to the direct proportional contribution of the measured area of the peaks): compound in which:

| | |
|---|---|
| n = 1 | 35.9% |
| n = 2 | 41.8% |
| n = 3 | 18.5% |
| n = 4 | 3.6% |

EXAMPLE 2: PREPARATION OF A COMPOUND OF FORMULA (I)

in which R=—CH$_2$A, A=—OR', R'=C$_{16}$H$_{33}$ and $\bar{n}$=1.5

The compound is prepared according to the procedure of Example 1, using:
—13.2 g (0.1 mol) of isopropylideneglycerol
—1.17 g (0.010 mol) of potassium tert-butylate
—44.7 g (0.15 mol) of hexadecyl glycidyl ether
—225 ml of isopropanol
—3.4 ml of concentrated HCl solution (d=1.19)

The product obtained is an amber-colored liquid which solidifies to give a wax having a melting point of 55° C.

Chromatographic analysis performed by the same method as in Example 1 shows that the product has the following composition: compound in which:

| | |
|---|---|
| n = 1 | 54.2% |
| n = 2 | 36.1% |
| n = 3 | 9.6% |

EXAMPLE 3: PREPARATION OF A COMPOUND OF FORMULA (I)

in which R=—CH$_2$A, A=—OR', R'=C$_{16}$H$_{33}$ and $\bar{n}$=2.5

The compound is prepared according to the procedure of Example 1, using:
—13.2 g (0.1 mol) of isopropylideneglycerol
—1.96 g (0.0175 mol) of potassium tert-butylate
—74.5 g (0.25 mol) of hexadecyl glycidyl ether
—200 ml of isopropanol
—3.96 ml of concentrated HCl solution (d=1.19)

The product obtained is, at room temperature, an amber-colored wax having a melting point of 51.6° C.

Chromatographic analysis performed by the same method as in Example 1 shows that the product obtained has the following composition: compound in which:

| | |
|---|---|
| n = 1 | 22.2% |
| n = 2 | 43.9% |
| n = 3 | 27.8% |
| n = 4 | 5.9% |

EXAMPLE 4: PREPARATION OF A COMPOUND OF FORMULA (I)

in which R=—CH$_2$A, A=—OR', R'=C$_{16}$H$_{33}$ and $\bar{n}$=3

The compound is prepared according to the procedure of Example 1, using:
—33 g (0.25 mol) of isopropylideneglycerol
—5.9 g (0.052 mol) of potassium tert-butylate
—223.5 g (0.75 mol) of hexadecyl glycidyl ether
—1 liter of isopropanol —11 ml of concentrated HCl solution (d=1.19)

The product obtained is, at room temperature, a light brown wax having a melting point of 51.9° C.

Chromatographic analysis performed by the same method as in Example 1 shows that the product obtained has the following composition: compound in which:

| | |
|---|---|
| n = 1 | 12% |
| n = 2 | 37% |
| n = 3 | 34% |
| n = 4 | 17% |

EXAMPLE 5: PREPARATION OF A COMPOUND OF FORMULA (I)

in which R=—$CH_2A$, A=—OR', R'=$C_{12}H_{25}$ and $\bar{n}$=3

The compound is prepared according to the procedure of Example 1, using:
—13.2 g (0.1 mol) of isopropylideneglycerol
—2.3 g (0.021 mol) of potassium tert-butylate
—72.6 g (0.3 mol) of dodecyl glycidyl ether
—350 ml of isopropanol
—4.25 ml of concentrated hydrochloric acid solution (d=1.18) and 5 ml of water A product which is a yellow oil is obtained.

Chromatographic analysis performed by the same method as in Example 1 shows that the product has the following composition: compound in which:

| | |
|---|---|
| n = 1 | 20% |
| n = 2 | 40% |
| n = 3 | 25% |
| n = 4 | 11% |
| n = 5 | 4% |

EXAMPLE 6: PREPARATION OF A COMPOUND OF FORMULA (I)

in which R=—$CH_2A$, A=—OR', R'=$C_8H_{17}$ and $\bar{n}$=4

The compound is prepared according to the procedure of Example 1, using:
—13.2 g (0.1 mol) of isopropylideneglycerol
—3.14 g (0.028 mol) of potassium tert-butylate
—74.4 g (0.4 mol) of octyl glycidyl ether
—350 ml of isopropanol
—4.8 ml of concentrated hydrochloric acid solution (d=1.18) and 5 ml of water In the second stage, the mixture is heated to reflux of the isopropanol for 2 hours.

The product obtained is a brown oil.

Chromatographic analysis performed by the same method as in Example 1 shows that the product has the following composition: compound in which:

| | |
|---|---|
| n = 1 | 25.9% |
| n = 2 | 34.1% |
| n = 3 | 21.5% |
| n = 4 | 11.5% |
| n = 5 | 10.7% |
| n = 6 | 7.0% |
| n = 7 to 12 | traces detectable |

EXAMPLE 7: PREPARATION OF A COMPOUND OF FORMULA (I)

in which R=—$CH_2A$, A=—OR', R'=$C_{10}H_{21}$ and $\bar{n}$=3

The compound is prepared according to the procedure of Example 1.

In the first stage, the following are mixed:
—13.2 g (0.1 mol) of isopropylideneglycerol
—2.3 g (0.021 mol) of potassium tert-butylate
The following are added:
—68 g (0.32 mol) of decyl glycidyl ether When the addition is complete, heating is maintained for 2 hours at 120° C. and then for 2 hours at 130° C. In the second stage, the following are added:
—350 ml of isopropanol
—4.3 ml of concentrated hydrochloric acid solution (d=1.18) and 5 ml of water The mixture is heated to reflux of the isopropanol for 3 hours.

The product obtained is a brown oil.

Chromatographic analysis performed by the same method as in Example 1 shows that the product has the following composition: compound in which:

| | |
|---|---|
| n = 1 | 34.3% |
| n = 2 | 42.0% |
| n = 3 | 17.7% |
| n = 5 | 5.8% |

EXAMPLE 8: PREPARATION OF A COMPOUND OF FORMULA (I)

in which R=—$CH_2A$, A=—OR', R'

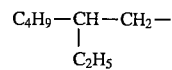

and $\bar{n}$=5

The compound is prepared according to the procedure of Example 1, using:
—13.2 g (0.1 mol) of isopropylideneglycerol
—3.9 g (0.035 mol) of potassium tert-butylate
—93 g (0.5 mol) of 2-ethylhexyl glycidyl ether
—400 ml of isopropanol
—5.4 ml of concentrated hydrochloric acid solution (d=1.18) and 5 ml of water In the second stage, the mixture is heated to reflux of the isopropanol for two hours.

The product obtained is a brown oil.

Chromatographic analysis performed by the same method as in Example 1 shows that the product has the following composition: compound in which:

| | |
|---|---|
| n = 1 | 10.0% |
| n = 2 | 25.0% |
| n = 3 | 21.0% |
| n = 4 | 14.5% |
| n = 5 | 11.0% |
| n = 6 | 11.0% |
| n = 7 | 7.5% |
| n = 8 to 13 | traces |

EXAMPLE 9: PREPARATION OF A COMPOUND OF FORMULA (I)

in which R=—$CH_2A$, A=—OR', R'=$C_{18}H_{37}$ and $\bar{n}$=2

The compound is prepared according to the procedure of Example 1.

In a first stage, the following are mixed:
—13.2 g (0.1 mol) of isopropylideneglycerol —1.57 g (0.014 mol) of potassium tert-butylate
The following are then added:
—65.2 g (0.2 mol) of octadecyl glycidyl ether When the addition is complete, heating is continued at 150° C. for 4 hours. 0.5 g of potassium tert-butylate is added to the mixture and heating is continued at 150° C. for 2 hours.

In a second stage, the following are added:
—300 ml of isopropanol
—4 ml of concentrated hydrochloric acid solution (d=1.18) and 4 ml of water The mixture is heated to reflux of the isopropanol for two hours.

The product obtained is a beige wax having a melting point of 59.1° C.

Chromatographic analysis is performed by the same method as in Example 1 shows that the product has the following composition: compound in which:

| | |
|---|---|
| n = 1 | 38% |
| n = 2 | 27% |
| n = 3 | 23% |
| n = 4 | 9% |
| n = 5 | 3% |

EXAMPLE 10: PREPARATION OF A COMPOUND OF FORMULA (I)

in which R=—CH$_2$A, A=—OR', R'=C$_3$—(CH$_2$)$_7$—CH=CH—(CH$_2$)$_8$—, $\bar{n}$=2

The compound is prepared according to the procedure of Example 1.
In a first stage, the following are mixed:
—6.6 g (0.05 mol) of isopropylideneglycerol
—1.57 g (0.014 mol) of potassium tert-butylate
The following are then added:
—32.4 g (0.1 mol) of oleyl glycidyl ether When the addition is complete, the reaction mixture is heated to 150° C. for 5 hours.

In a second stage, the following are added:
—150 ml of isopropanol
—2.5 ml of concentrated hydrochloric acid solution (d=1.18) and 2.5 ml of water The mixture is heated to 80° C. for 4 hours.
The product obtained is a brown oil.
The $^{13}$C NMR spectrum is in agreement with the formula.

Chromatographic analysis performed by the same method as in Example 1 shows that the product has the following composition: compound in which:

| | |
|---|---|
| n = 1 | 27% |
| n = 2 | 37% |
| n = 3 | 26% |
| n = 4 | 8% |
| n = 5 | 2% |

EXAMPLE 11: PREPARATION OF A COMPOUND OF FORMULA (I)

in which R=—CH$_2$A, A=—OR', R'=isostearyl(*) $\bar{n}$=2 (*) the isostearyl radical is a mixture of isomeric C$_{18}$ alkyl radicals.

The compound is prepared according to the procedure of Example 1.
In the first stage, the following are mixed:
—13.2 g ( 0.1 mol ) of isopropylideneglycerol
—3.0 g ( 0.027 mol ) of potassium tert-butylate The following are then added:
—70 g (0.2 mol) of isostearyl glycidyl ether After the addition, the mixture is heated to 150° C. for 5 hours.

In the second stage, the following are added:
—350 ml of isopropanol, and
—4.2 ml of concentrated HCl solution (d=1.18)
The mixture is heated to 60° C. for 4 hours.
The product obtained is a brown oil.

Chromatographic analysis performed by the same method as in Example 1 shows that the product has the following composition: compound in which:

| | |
|---|---|
| n = 1 | 27% |
| n = 2 | 44% |
| n = 3 | 21% |
| n = 4 | 6% |
| n = 5 | 2% |

EXAMPLE 12: PREPARATION OF A COMPOUND OF FORMULA (I)

in which R=—CH$_2$A, A=—OR',

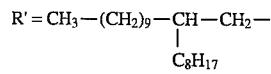

R' = CH$_3$—(CH$_2$)$_9$—CH—CH$_2$—
                              |
                              C$_8$H$_{17}$ and $\bar{n}$=2

The compound is prepared according to the procedure of Example 1.
In the first stage, the following are mixed:
—13.2 g (0.1 mol) of isopropylideneglycerol
—2.25 g (0.02 mol) of potassium tert-butylate
The following are then added:
—70.8 g (0.2 mol) of 2-octyldodecyl glycidyl ether When the addition is complete, heating is continued at 150° C. for 2 hours.

In the second stage, the following are mixed:
—350 ml of isopropanol, and
—4.2 ml of concentrated HCl solution(d=1.18)
The mixture is heated to 80° C. for 4 hours.
The product obtained is a brown oil.

Chromatographic analysis performed by the same method as in Example 1 shows that the product has the following composition: compound in which:

| | |
|---|---|
| n = 1 | 22% |
| n = 2 | 40% |
| n = 3 | 29% |
| n = 4 | 9% |

EXAMPLE 13: PREPARATION OF A COMPOUND OF FORMULA (I)

in which R=—CH$_2$A, A=—OR',

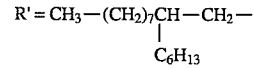

R' = CH$_3$—(CH$_2$)$_7$CH—CH$_2$—
                            |
                            C$_6$H$_{13}$ and $\bar{n}$=2

The compound is prepared according to the procedure of Example 1.
In the first stage, the following are mixed:
—13.2 g (0.1 mol) of isopropylideneglycerol, and
—4.4 g (0.04 mol) of potassium tert-butylate The following are then added:
—59.6 g (0.2 mol) of 2-hexyldecyl glycidyl ether
When the addition is complete, heating is continued at 150° C. for 6 hours.
In the second stage, the following are added:
—350 ml of isopropanol
—7.5 ml of concentrated hydrochloric acid solution (d=1.18)
The mixture is heated to 80° C. for 2 hours.
The product obtained is a brown oil.
Chromatographic analysis performed by the same method as in Example 1 shows that the product has the following composition: compound in which:

| | |
|---|---|
| n = 1 | 19.0% |
| n = 2 | 23.0% |
| n = 3 | 25.0% |
| n = 4 | 15.0% |
| n = 5 | 9.5% |
| n = 6 | 4.5% |
| n = 7 | 3.0% |
| n = 8 | 1.0% |

EXAMPLE 14: PREPARATION OF A COMPOUND OF FORMULA (I)

in which R=—CH$_2$A, A=—OR',

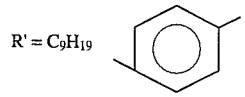

R' = C$_9$H$_{19}$ and $\bar{n}$=2

The compound is prepared according to the procedure of Example 1.
In the first stage, the following are mixed:
—13.2 g (0.1 mol) of isopropylideneglycerol, and
—3.3 g (0.03 mol) of potassium tert-butylate
The following are then added:
—56 g (0.2 mol) of nonylphenyl glycidyl ether
When the addition is complete, heating is continued at 150° C. for 2 hours.
In the second stage, the following are added:
—300 ml of isopropanol
—5 ml of concentrated hydrochloric acid solution (d=1.19)
The mixture is heated to reflux of the isopropanol for 2 hours.
The product obtained is a very viscous brown oil.
Chromatographic analysis performed by the same method as in Example 1 shows that the product has the following composition: compound in which:

| | |
|---|---|
| n = 1 | 15% |
| n = 2 | 32% |
| n = 3 | 31% |
| n = 4 | 16% |
| n = 5 | 6% |
| n = 6 | traces |

EXAMPLE 15: PREPARATION OF A COMPOUND OF FORMULA (I)

in which R=C$_{10}$H$_{21}$; $\bar{n}$=3
The compound is prepared according to the procedure of Example 1.
In the first stage, the following are mixed:
—13.2 g (0.1 mol) of isopropylideneglycerol and
—6.74 g (0.06 mol) of potassium tert-butylate
The following are then added:
—55.2 g (0.3 mol) of 1,2-epoxydodecane
After the addition, heating is continued at 180° C. for 6 hours.
In the second stage, the following are added:
—300 ml of isopropanol, and
—15 ml of 6N hydrochloric acid solution
The mixture is heated to reflux of the solvent for 3 hours.
Chromatographic analysis performed by the same method as in Example 1 shows that the product has the following composition: compound in which:

| | |
|---|---|
| n = 1 | 22% |
| n = 2 | 45% |
| n = 3 | 25% |
| n = 4 | 8% |

EXAMPLE 16: PREPARATION OF THE COMPOUND OF FORMULA (I)

in which R=C$_{12}$H$_{25}$ and $\bar{n}$=3
The compound is prepared according to the procedure of Example 1.
In the first stage, the following are mixed:
—13.2 g (0.1 mol) of isopropylideneglycerol and
—2.36 g (0.021 mol) of potassium tert-butylate
The following are then added:
—63.6 g (0.3 mol) of 1,2-epoxytetradecane
After the addition, heating is continued for 2 hours at 140° C. 2.36 g of potassium tert-butylate are then added and heating is continued for 4 hours at 140° C.
In the second stage, the following are added:
—300 ml of isopropanol, and
—15 ml of 6N hydrochloric acid solution
The mixture is heated to reflux of the solvent for 3 hours.
71.5 g of a waxy yellow product are obtained.
Chromatographic analysis performed by the same method as in Example 1 shows that the product has the following composition: compound in which:

| | |
|---|---|
| n = 1 | 17% |
| n = 2 | 40% |
| n = 3 | 23% |
| n = 4 | 9% |
| n = 5 | 4% |
| n = 6 | 4% |
| n = 7 | 3% |

EXAMPLE 17: PREPARATION OF A COMPOUND OF FORMULA (I)

in which R=C$_{14}$H$_{29}$ and $\bar{n}$=2
The compound is prepared according to the procedure of Example 1.
In the first stage, the following are mixed:
—33 g (0.25 mol) of isopropylideneglycerol and
—3.92 g (0.035 mol) of potassium tert-butylate
The following are then added:
—132 g (0.50 mol) of 1,2-epoxyhexadecane
After the addition, the mixture is heated to 140° C. for 2 hours.
In the second stage, the following are added:
—660 ml of isopropanol and
—7.35 ml of hydrochloric acid solution (d=1.18)

The mixture is maintained for 4 hours at 60° C.

127.5 g of a light brown product are obtained.

Chromatographic analysis performed by the same method as in Example 1 shows that the product has the following composition: compound in which:

| | |
|---|---|
| n = 1 | 37% |
| n = 2 | 40% |
| n = 3 | 17% |
| n = 4 | 6% |

EXAMPLE 18: PREPARATION OF A COMPOUND OF FORMULA (I)

in which R=$C_{14}H_{29}$ and $\bar{n}$=3

The compound is prepared according to the procedure of Example 1.

In the first stage, the following are mixed:
—33 g (0.25 mol) of isopropylideneglycerol and
—5.9 g (0.052 mol) of potassium tert-butylate The following are then added:
—180 g (0.75 mol) of 1,2-epoxyhexadecane After the addition, heating is continued at 140° C. for 2 hours.

In the second stage, the following are added:
—1 liter of isopropanol and
—11 ml of concentrated hydrochloric acid The mixture is heated to 60° C. for 4 hours.

174 g of a light brown product are obtained.

Chromatographic analysis performed by the same method as in Example 1 shows that the product has the following composition: compound in which:

| | |
|---|---|
| n = 1 | 20% |
| n = 2 | 44% |
| n = 3 | 24% |
| n = 4 | 6% |
| n = 5 | 6% |

EXAMPLE 19: PREPARATION OF A COMPOUND OF FORMULA (I)

in which R=$C_{16}H_{33}$ and $\bar{n}$=2

The compound is prepared according to the procedure of Example 1.

In the first stage, the following are mixed:
—9.9 g (0.075 mol) of isopropylideneglycerol, and
—1.77 g (0.016 mol) of potassium tert-butyl The following are then added:
—40.2 g (0.15 mol) of 1,2-epoxyoctadecane When the addition is complete, heating is continued at 180° C. for 4 hours.

In the second stage, the following are added:
—300 ml of isopropanol and
—3.71 ml of concentrated hydrochloric acid The mixture is heated to 80° C. for 2 hours.

44 g of a brown product are obtained.

Chromatographic analysis performed by the same method as in Example 1 shows that the product has the following composition: compound in which:

| | |
|---|---|
| n = 1 | 48% |
| n = 2 | 38% |
| n = 3 | 8% |
| n = 4 | 6% |

EXAMPLE 20: PREPARATION OF A COMPOUND OF FORMULA (I)

in which R is a mixture of $C_{22}$–$C_{26}$ alkyl radicals.

The compound is prepared according to the procedure of Example 1.

In the first stage, the following are mixed:
—13.2 g (0.1 mol) of isopropylideneglycerol, and
—1.57 g (0.014 mol) of potassium tert-butylate The following are then added:
—85.4 g (0.2 mol) of "VIKOLOX 24–28" (which is a mixture of epoxides of the formula (III) in which R is a mixture of $C_{22}$ to $C_{26}$ radicals, marketed by the company VIKING). Heating is maintained for 4 hours at 140° C.

A further 1.57 g of potassium tert-butylate are added and heating is continued at 140° C. for 4 hours.

In the second stage, the following are added:
—300 ml of isopropanol and
—6 ml of concentrated hydrochloric acid The mixture is heated for 4 hours to reflux of the solvent.

63 g of a beige product are obtained, which product solidifies at room temperature and has a melting point of 75°–80° C.

EXAMPLE 21: PREPARATION OF THE COMPOUNDS OF FORMULA I in which R=—$CH_2A$, A=OR', R'=$C_{16}H_{33}$ and n=1 (not included in the invention) and n=2.

Hexadecyl glycidyl ether (50 g; 0.17 mol) is solubilized in 44.25 g, (3.35 mol) of isopropylideneglycerol. Separately, 44.25 g (3.35 mol) of isopropylideneglycerol are introduced into a reactor with 1.5 g (0.013 mol) and of potassium tert-butylate. The reaction medium is heated to 140° C. and, at this temperature, the solution of hexadecyl glycidyl ether in isopropylideneglycerol is introduced in the course of 2 hours. The mixture is heated for a further hour at 140° C. after the addition. After cooling, 120 ml of NaCl solution (10 g in 150 ml of water) are added. Settling is allowed to take place, and the aqueous phase is removed; 350 ml of hexane are added to the organic phase. Settling is allowed to take place again. A small brown phase is removed. The organic phase is then dried over sodium sulfate. The solvent is removed under a reduced pressure of $53\times10^2$ pascals, and the isopropylideneglycerol is then removed under a reduced pressure of $1.3\times10^2$ pascals.

The final product is collected in a 94% yield.

This product is subjected to a distillation at 150° C.

The compound in which n=1 is isolated from among light products in a 90% yield; it is a clear, almost colorless oil which solidifies at room temperature.

The heavy products essentially contain the compound in which n=2. They are dissolved in methanol under reflux and then treated with concentrated hydrochloric acid (589 g of residue, 53 ml of 5N HCl and 250 ml of methanol). The mixture is maintained under reflux for 3 hours; it is then allowed to cool overnight.

The precipitate is collected by filtration, then dissolved in ethyl acetate and filtered in the hot state to remove insoluble matter (250 ml of ethyl acetate for 50 g of crude product). The product is left to crystallize overnight at 8° C. and then filtered off on sintered glass. The drained cake is recrystallized a second time in 200 ml of solvent.

After drying, 24.7 g of a light beige powder are obtained, having a melting point of 54.1° C.

Analysis by supercritical fluid chromatography and flame ionization detection indicates the residual presence of 7% by weight of compound in which n=1 and 6.5% of compound in which n=3, the remainder consisting of the compound in which n=2 (the percentages corresponding to the proportional contribution of the measured area of the peaks).

EXAMPLES 22 TO 29: FORMULATIONS

EXAMPLE 22 (comparative)

Vesicle dispersions were prepared from nonionic amphiphilic compounds of formula (I) according to the invention in which n has various values, R is $C_{14}H_{29}$ or R is —$CH_2A$, A being —OR', R' being $C_{16}H_{33}$, and, for comparison, with three nonionic amphiphilic compounds not forming part of the invention, of formula:

$$C_{16}H_{33}-O+C_2H_3O-(CH_2OH)\overline{_3}H \quad (F1)$$

—$C_2H_3O(CH_2OH)$— representing the following structures, taken mixed or separately:

(F2)

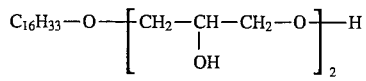

and

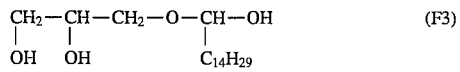
(F3)

containing a single lipophilic chain.

1) PREPARATION OF THE VESICULAR PHASES

The following products are weighed into a glass beaker:

| | |
|---|---|
| nonionic amphiphilic compound | 9.00 g |
| cholesterol | 5.25 g |
| dicetyl phosphate | 0.75 g |

The mixing of these three products is carried out by melting at a temperature of 100° C. under a nitrogen atmosphere. The temperature of the molten mixture is then lowered to 90° C.

30 g of demineralized water are added and the mixture obtained is homogenized at a temperature of 90° C.

i) To a first fraction of the product obtained, corresponding to 15 g of lipids, demineralized water is added and the mixture is dispersed at 70° C. using a "VIRTIS" type ultradisperser for 4 minutes at a speed of 40000 rpm, so as to obtain a dispersion (c) of vesicles containing 15% by weight of lipids; the vesicles are not loaded with active products. The viscosity of the vesicle dispersion (c) is then measured at least 18 hours after its manufacture.

ii) To a second fraction of the product obtained, corresponding to 15 g of lipids, 5.57 g of glycerol and 24 g of demineralized water are added.

At a temperature of 70° C., the mixture is homogenized using a "VIRTIS" type ultradisperser for 4 minutes at a speed of 40000 rpm.

The following are then added:

—13.94 g of an aqueous solution containing 20% by weight of poly-β-alanine;

—9.3 g of an aqueous solution containing 1% by weight of monomethyltrisilanol lactate sold by the company Jean D'AVEZ under the trade name "LASILIUM";

—0.56 g of stabilizer consisting of diazolidinylurea sold by the company SUTTON under the trade name "GERMALL II";

—0.56 g of stabilizer consisting of a mixture of methylchloroisothiazolinone and methylisothiazolinone, sold by the company ROHM and HAAS under the trade name "KATHON CG", dissolved in 1 g of demineralized water.

At a temperature of 40° C., the mixture is homogenized using a "VIRTIS" ultradisperser for 2 minutes at a speed of 40000 rpm.

It is found that, with the product of formula ($F_3$) not forming part of the invention, it is not possible to obtain vesicles under the conditions used.

With the other compounds, a dispersion (a) of vesicles loaded with active products, of sizes smaller than 0.3 micron, is obtained, the viscosity of which is measured at least 18 hours after manufacture.

2) ADDITION OF A FATTY PHASE FOR THE PREPARATION OF A CREAM

The following are added to the dispersion (a) of vesicles loaded with active products:

—27.9 g of macadamia oil; and

—18.6 g of volatile silicone oil.

At a temperature of 30° C., the whole is homogenized using a "VIRTIS" type ultradisperser for 4 minutes at a speed of 40000 rpm. A thick white cream (b) is thereby obtained, the viscosity of which is measured at least 18 hours after manufacture.

The results of the various viscosity measurements are given in Table I below.

TABLE I

| NONIONIC AMPHIPHILIC COMPOUND | NUMBER OF LIPOPHILIC CHAINS | VISCOSITY OF THE DISPERSION (a) (pascal seconds) | VISCOSITY OF THE DISPERSION (c) (pascal seconds) | VISCOSITY OF THE CREAM (b) (pascal seconds) |
|---|---|---|---|---|
| $C_{16}H_{33}O+C_2H_3O-(CH_2OH\overline{_3}H$ * | 1 | 0.02 | — | 0.11 |
| $C_{16}H_{33}O+CH_2-CH-CH_2-O\overline{_{12}}H$ *<br>\|<br>OH | 1 | 0.02 | 2.4 | 0.15 |

TABLE I-continued

| NONIONIC AMPHIPHILIC COMPOUND | NUMBER OF LIPOPHILIC CHAINS | VISCOSITY OF THE DISPERSION (a) (pascal seconds) | VISCOSITY OF THE DISPERSION (c) (pascal seconds) | VISCOSITY OF THE CREAM (b) (pascal seconds) |
|---|---|---|---|---|
| HO$+$CH—CH$_2$$\frac{}{n}$OCH$_2$—CH—CH$_2$OH<br>⎮       ⎮<br>CH$_2$      OH<br>⎮<br>O—C$_{16}$H$_{33}$ | $\overline{1.5}$ (ex 2)<br>$\overline{2}$ (ex 1)<br>$\underline{2}$ (ex 21)<br>$\overline{2.5}$ (ex 3)<br>$\overline{3}$ (ex 4) | 0.2<br>1<br>0.3<br>0.4<br>0.13 | —<br>2<br>—<br>—<br>— | 0.60<br>0.66<br>0.94<br>2.33<br>3.75 |
| HO$+$CH—CH$_2$]$_n$O—CH$_2$—CH—CH$_2$OH<br>⎮               ⎮<br>C$_{14}$H$_{32}$          OH | $\overline{2}$ (ex 17)<br>$\overline{3}$ (ex 18) | 0.10<br>0.70 | —<br>— | 0.30<br>0.66 |

*Does not form part of the invention

In this table, it is seen that the dispersions of vesicles loaded with active products, prepared from amphiphilic compounds having several fatty chains according to the invention, possess a higher viscosity than those obtained from vesicles containing amphiphilic compounds having a single chain; that the viscosity of the same vesicles not loaded with an active compound dissolved in water is of the same order of magnitude; and that, in contrast, the viscosity in the presence of a fatty phase is markedly higher. The amphiphilic compounds having several lipophilic chains hence limit, in the creams, the fluidizing effect of the cosmetic active compounds used.

EXAMPLE 23—Anti-aging day cream for the face

1st phase: Preparation of the vesicle dispersion

The following products are weighed into a glass beaker:

| | |
|---|---|
| nonionic amphiphilic lipid of Example 17 | 4.8 g |
| cholesterol | 2.8 g |
| dicetyl phosphate | 0.4 g |

The mixing of the lipids is carried out by melting at a temperature of 100° C. under a nitrogen atmosphere. The temperature of the molten mixture is then lowered to 90° C. 27.0 g of demineralized water are added and the mixture obtained is homogenized at a temperature of 90° C.

The following compounds are then added:

| | |
|---|---|
| glycerol | 3.0 g |
| L-hydroxyproline | 1.0 g |
| D-panthenol | 1.5 g |
| guanosine | 0.01 g |
| preservative q.s. | |
| aqueous solution containing 20% of poly-β-alanine, prepared according to patent FR-A-2, 508,795 | 7.5 g |
| polyphosphonate marketed by the company MONSANTO CHEMICAL under the name "DEQUEST 2046" | 0.8 g |
| lactic hydrolysate marketed by the company LABORATOIRES SEROBIOLOGIQUES under the name "LACTOLAN LS" | 5.0 g |
| L-serine | 0.2 g |

At a temperature of 70° C., the mixer is homogenized using a "VIRTIS" type ultradisperser for 4 minutes at a speed of 40000 rpm. A vesicle dispersion is thereby obtained.

2nd phase: Formulation of the cream

The following substances are added to the dispersion obtained:

| | |
|---|---|
| propyl para-hydroxybenzoate | 0.05 g |
| macadamia oil | 7.0 g |
| natural concentrates of tocopherols, marked by the company PROCHIMEX | 4.0 g |
| 2-ethylhexyl methoxycinnamate marketed by the company GIVAUDAN under the name "PARSOL MCX" | 0.5 g |
| 2-hydroxy-4-methoxybenzophenone marketed by the company BASF under the name "UVINUL M 40" | 0.5 g |
| volatile silicone oil | 7.5 g |
| vitamin F glycerides marketed by the company DUBOIS | 3.0 g |
| aqueous solution of superoxide dismutase, sold by the company PENTAPHARM at a concentration of 5000 units per ml | 1.0 g |
| perfume | 0.2 g |
| crosslinked polyacrylic acid marketed by the company GOODRICH under the name "CARBOPOL 940" | 0.5 g |
| methyl para-hydroxybenzoate | 0.2 g |
| L-lysine monohydrate | 1.0 g |
| water q.s. | 100.0 g |

At a temperature of 40° C., the mixture is homogenized using a "VIRTIS" ultradisperser for 2 minutes at a speed of 40000 rpm. A cream is thereby obtained, having a viscosity of 6 pascal seconds and a pH of 6.5.

The lipid of Example 17 may be replaced by those of Examples 1 or 18.

EXAMPLE 24: HYDRATING DAY CREAM FOR THE FACE

The cream is prepared as in Example 23.

In the 1st phase, a vehicle dispersion having the following composition is prepared:

| | |
|---|---|
| nonionic amphiphilic lipid of Example 1 | 3.6 g |
| cholesterol | 2.1 g |
| dicetyl phosphate | 0.3 g |
| alpha-tocopherol acetate | 0.3 g |
| glycerol | 5.0 g |
| water | 35.0 g |
| stabilizer consisting of a mixture of methylchloroisothiazolinone and methyl-isothiazolinone, sold by the company ROHM and HAAS under the name "KATHON CG" | 0.05 g |
| stabilizer consisting of diazolidinylurea, | 0.3 g |

-continued

| | |
|---|---|
| sold by the company SUTTON under the trade name "GERMALL II" | 0.3 g |
| citric acid | 0.02 g |
| water | 1.0 g |

In the 2nd phase, the following compounds are added to the dispersion:

| | |
|---|---|
| macadamia oil | 10.0 g |
| octyldodecanol sold by the company HENKEL under the name "EUTANOL G" | 5.0 g |
| volatile silicone oil | 5.0 g |
| 2-ethylhexyl methoxycinnamate marketed by the company GIVAUDAN under the name "PARSOL MCX" | 0.5 g |
| 2-hydroxy-4-methoxybenzophenone marketed by the company BASF under the name "UVINUL M 40" | 0.5 g |
| propyl para-hydroxybenzoate | 0.05 g |
| crosslinked polyacrylic acid marketed by the company GOODRICH under the name "CARBOPOL 940" | 0.5 g |
| methyl para-hydroxybenozate | 0.2 g |
| triethanolamine | 0.48 g |
| water q.s. | 100 g |

EXAMPLE 25

A lipstick having the following composition is prepared:

| | |
|---|---|
| ozokerite | 12.0 g |
| microcrystalline wax | 4.0 g |
| candellila wax | 6.0 g |
| compound of Example 9 | 5.0 g |
| jojoba oil | 10.0 g |
| castor oil | 20.0 g |
| lanolin | 15.0 g |
| acetylated lanolin | 9.0 g |
| liquid paraffin | 9.0 g |
| D and C Red 7 calcium lake | 4.2 g |
| D and C Red 7 barium lake | 2.3 g |
| FDC Yellow 5 | 0.8 g |
| titanium dioxide | 2.5 g |
| butylated hydroxytoluene | 2.0 g |
| perfume q.s. | |

The oils are mixed at a temperature of 50° to 60° C. The pigments and organic lakes are ground in the oily phase.

The molten waxes are then added, followed by the perfume.

The composition is then cast in a mold.

EXAMPLE 26

A water-in-oil emulsion is prepared in the following manner:

The following are mixed by heating at 80° C.:
—25 g of paraffin oil
—2 g of polyoxyethylenated sorbitan monooleate containing 20 mol of EO, sold by the company ICI under the name "TWEEN 80"
—2 g of the compound of Example 11.

71 g of distilled water, heated to 70° C., are added slowly with agitation. The mixture is allowed to cool to room temperature with vigorous agitation for 10 minutes.

A fine, homogeneous and stable water-in-oil emulsion is obtained.

EXAMPLE 27: AFTER-SHAVE BALM

In a first stage, a vesicular dispersion is prepared in the following manner:

The mixing of the following products is carried out by melting at a temperature of 90°–95° C.:

| | |
|---|---|
| lipid of Example 17 | 1.9 g |
| monosodium stearoylglutamate sold by the company AJINOMOTO under the name "ACYL GLUTAMATE HS 11" | 0.2 g |
| cholesterol | 1.9 g |

8 g of demineralized water are added and the mixture obtained is homogenized.

The following compounds are then added at room temperature:

| | |
|---|---|
| methyl para-hydroxybenzoate | 0.1 g |
| 1,3-dimethylol-5,5-dimethylhydantoin sold by the company GLYCO under the name "GLYDANT" | 0.055 g AS |
| demineralized water | 12.0 g |

The mixture is agitated to obtain a vesicle dispersion.

The following substances are added to obtain the balm:

| | |
|---|---|
| protected liquid lanolin sold by the company STELLA under the name "STELLANOL" | 1.0 g |
| α,ω-dihydroxylated polydimethylsiloxane/ cyclotetradimethylsiloxane/cyclopenta-dimethylsiloxane (14:48.2:37.8) mixture sold by the company DOW CORNING under the name "DOW CORNING QCF-1671" | 5.0 g |
| perfume | 0.5 g |
| carboxyvinyl polymer sold by GOODRICH under the name "CARBOPOL 940" | 0.2 g |
| triethanolamine qs pH 6.5 | |
| demineralized water qs | 100.0 g |

It is found that, in the balm, the vesicles remain stable.

EXAMPLE 28: SELF-TANNING CREAM

A cream containing nonionic lipid vesicles having the following composition is prepared as in Example 27:

| | |
|---|---|
| lipid of Example 17 | 3.8 g |
| cholesterol | 3.8 g |
| monosodium stearoylglutamate sold by the company AJINOMOTO under the name "ACYL GLUTAMATE HS 11" | 0.4 g |
| demineralized water | 16.0 g |
| glycerol | 2.0 g |
| dihydroxyacetone | 5.0 g |
| preservatives qs | |
| demineralized water | 24.0 g |
| liquid paraffin sold by the company GEERAERT MATTHYS under the name "SIDEPALINE BC 15" | 15.0 g |
| perfume qs | |
| hydrophobic hydroxyethylcellulose sold by the company AQUALON under the name "NATROSOL PLUS GRADE 330 CS" | 0.5 g |
| demineralized water qs | 100.0 g |

It is found that the vesicles remain stable in the cream.

The lipid of Example 17 could be replaced by that of Example 1.

EXAMPLE 29: SUN CREAM

A cream containing nonionic lipid vesicles is prepared as in Example 27.

| | |
|---|---|
| lipid of Example 1 | 4.8 g |
| cholesterol | 2.8 g |
| monosodium stearoylglutamate sold by the company AJINOMOTO under the name ACYL GLUTAMATE HS 11" | 0.4 g |
| demineralized water | 16.0 g |
| preservatives qs | |
| demineralized water | 24.0 g |
| liquid paraffin sold by company "GEERAERT MATTHYS under the name "SIDEPALINE BC 15" | 15.0 g |
| 2-ethylhexyl para-methoxycinnamate sold by the company GIVAUDAN under the name "PARSOL MCX" | 4.0 g |
| | 4.0 g |
| 2-hydroxy-4-methoxybenzophenone sold by the company BASF under the name "UVINUL M40" | 2.0 g |
| perfume qs | |
| carboxyvinyl polymer sold by the company GOODRICH under the name "CARBOPOL 940" | 0.4 g |
| demineralized water qs | 100.0 g |

It is found that, in the cream, the vesicles remain stable.

We claim:

1. A nonionic amphiphilic compound having the formula

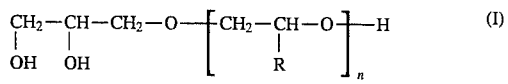

wherein

R represents a radical selected from the group consisting of
(i) a linear or branched $C_4$–$C_{28}$ alkyl or alkenyl, or a mixture thereof, and
(ii) —$CH_2A$ wherein A represents —OR', —SR' or

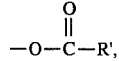

wherein R' represents a saturated or unsaturated hydrocarbon, and n represents an average statistical value $\bar{n}$ greater than 1 and equal to not more than 6 and, when R represents —$CH_2A$, n also represents a value equal to 2.

2. The compound of claim 1 wherein R' represents a member selected from the group consisting of linear $C_8$–$C_{22}$ alkyl, branched $C_8$–$C_{36}$ alkyl, $C_{18}$ alkenyl and alkylaryl wherein said alkyl moiety is a linear or branched $C_8$–$C_{16}$ alkyl.

3. The compound of claim 2 wherein the aryl moiety is phenyl.

4. The compound of claim 2 wherein said $C_{18}$ alkenyl is 9-octadecenyl or 9,12-octadecanedienyl.

5. The compound of claim 1 wherein
R represents linear $C_{14}$–$C_{18}$ alkyl or
—$CH_2A$ wherein A represents OR' wherein R' represents linear $C_{10}$–$C_{18}$ alkyl, and
n represents an average statistical value $\bar{n}$ greater than 1 and equal to not more than 3 and, when R represents —$CH_2A$, n also is equal to 2.

6. A process for preparing a compound having a formula

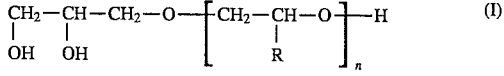

wherein

R represents a radical selected from the group consisting of
(i) a linear or branched $C_4$–$C_{28}$ alkyl or alkenyl, or a mixture thereof, and
(ii) —$CH_2A$ wherein A represents —OR', —SR' or

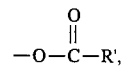

wherein R' represents a saturated or unsaturated hydrocarbon, and n represents an average statistical value $\bar{n}$ greater than 1 and equal to not more than 6 and, when R represents —$CH_2A$, n also represents a value equal to 2, said process comprising a two-stage process, said first stage comprising reacting an isopropylideneglycerol having the formula

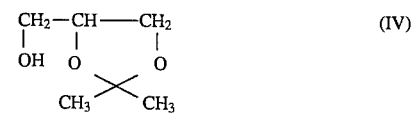

in the presence of a basic catalyst, with an epoxide of formula III

wherein R and n have the meanings given above, so as to produce an intermediate product having the formula II

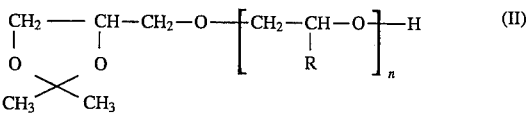

wherein R and n have the meanings given above, and in a second stage hydrolyzing said intermediate product of formula II so as to produce said compound of formula I and separating therefrom said compound of formula I.

7. The process of claim 6 wherein said basic catalyst in said first stage is selected from the group consisting of an alkali metal, an alkali metal hydride, an alkali metal hydroxide, an alkali metal alcoholate and an alkali metal fluoride.

8. The process of claim 7 wherein said basic catalyst is potassium tert.-butylate.

9. The process of claim 6 wherein, in said first stage, at least a portion of said isopropylideneglycerol of formula (IV) and said basic catalyst are mixed under an inert atmosphere, the resulting mixture being heated to a temperature ranging from 50° to 150° C. and adding said epoxide of formula III.

10. The process of claim 6 wherein, in said second stage, said intermediate product of formula II is hydrolyzed in the presence of an acid catalyst.

11. The process of claim 10 wherein, in said second stage, said intermediate product of formula II is hydrolyzed in the presence of a solvent.

12. A nonionic compound of formula II

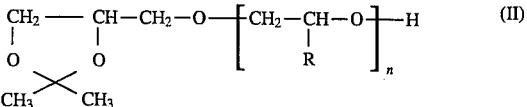

wherein

R represents a radical selected from the group consisting of (i) a linear or branched $C_4$–$C_{28}$ alkyl or alkenyl, or a mixture thereof, and
(ii) —$CH_2A$ wherein A represents —OR', —SR' or
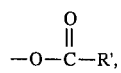
wherein R' represents a saturated or unsaturated hydrocarbon, and
n represents an average statistical value $\bar{n}$ greater than 1 and equal to not more than 6 and, when R represents —$CH_2A$, n also represents a value equal to 2.
* * * * *